United States Patent [19]

Cosand

[11] Patent Number: 4,629,783

[45] Date of Patent: Dec. 16, 1986

[54] SYNTHETIC ANTIGEN FOR THE DETECTION OF AIDS-RELATED DISEASE

[75] Inventor: Wesley L. Cosand, Bothell, Wash.

[73] Assignee: Genetic Systems Corporation, Seattle, Wash.

[21] Appl. No.: 767,303

[22] Filed: Aug. 19, 1985

Related U.S. Application Data

[63] Continuation-in-part of Ser. No. 728,052, Apr. 29, 1985, abandoned.

[51] Int. Cl.[4] .......................... C07K 7/10; C07K 17/00

[52] U.S. Cl. .................................... 530/324; 530/325; 530/326; 530/403

[58] Field of Search ................. 260/112.5 R; 530/324, 530/325, 326, 403

[56] References Cited

PUBLICATIONS

J. Biochem. 91 201–210 (1982).
Molecular Immunology 18, (1981) 869–872.
Nature 312 (1984) 127–134.

*Primary Examiner*—Delbert R. Phillips
*Attorney, Agent, or Firm*—Leydig, Voit & Mayer

[57] ABSTRACT

Novel peptides are provided having substantially the same sequence as immunologically significant fragments of AIDS-related viruses. The polypeptides can be used as reagents in the determination of exposure of a human host to the virus. Of particular interest is the use of polypeptides in screening blood products.

7 Claims, No Drawings

SYNTHETIC ANTIGEN FOR THE DETECTION OF AIDS-RELATED DISEASE

BACKGROUND OF THE INVENTION

Field of the Invention

With the discovery that the diseases called lymphadenopathy syndrome and acquired immune deficiency disease (AIDS) are caused by an infectious retrovirus designated lymphadenopathy virus (LAV), human T-cell lymphotropic virus-III (HTLV-III), AIDS-related virus (ARV), or immune deficiency-associated virus (IDAV), there has become an immediate need to be able to detect potential vectors of the disease, such as blood from diseased individuals, which may be employed for transfusions or from which specific blood factors may be isolated.

To detect potential vectors of the disease, it is necessary to have viral proteins and/or antibodies to such proteins. Because of the hazards associated with growing the LAV/HTLV-III retrovirus, there is significant interest in establishing means for obtaining the viral proteins or their immunologic equivalents, which means do not necessitate handling large volumes of live, potentially infectious virus. In choosing alternatives, one must be concerned with the fact that the viruses have been reported to be highly polymorphic, frequently changing as the retrovirus is passaged.

Brief Description of the Relevant Literature

The various antigens of the retrovirus are described by Saxinger et al., *Science* (1985) 227:1036-1038. See also Gallo et al., ibid. (1984) 224:500; Sarangadharn et al., ibid. 224:506; Barre-Sinoussi et al., ibid. (1983) 220:868; Montagnier et al., in Human T-Cell Leukemia/Lymphoma Virus, Gallo, Essex, Gross, eds. (Cold Spring Harbor Laboratory, Cold Spring Harbor, N.Y.), 1984, p. 363. These may include, but are not limited to, p13, p18, p25, p36, gp43, p55, gp65, gp110, etc., where the numbers may differ depending upon the reporter.

Hopp and Woods, *Proc. Natl. Acad. Sci. USA* (1981) 78:3824, describe criteria for selecting peptides as potential epitopes of polypeptides based on their relative hydrophilicity. In one study employing these criteria, a 12-amino acid peptide was synthesized that bound 9% of antibodies elicited by the native protein (Hopp, *Molec. Immunol.* (1981) 18:869). In general, Hopp/Woods criteria have been shown not to have a high predictive value. Furthermore, epitopes have been demonstrated which are not hydrophilic (Kazim et al., *Biochem. J.* (1982) 203:201). Other studies of polypeptide antigenicity include Green et al., *Cell* (1982) 28:477, where peptides were employed which elicited antibodies, which antibodies were capable of binding to the native protein, while conversely antibodies which were elicited by the native protein failed to bind to the peptides; and Trainer et al., *Nature* (1984) 312:127, whose results with myohaemerythrin paralleled those of Green et al.

The complete nucleotide sequence of LAV is reported by Wain-Hobson et al., *Cell* (1985) 40:9. The complete sequence for HTLV-III is reported by Muesing et al., *Nature* (1985) 313:450, while the complete sequence for ARV is reported by Sanchez-Pescador et al., *Science* (1985) 227:484. All three viruses exhibit substantial nucleotide homology and are similar with respect to morphology, cytopathology, requirements for optimum reverse transcriptase activity, and at least some antigenic properties (Levy et al., *Science* (1984) 225:840; Shupbach et al., *Science* (1984) 224:503), and hence should be considered isolates of the same virus. See also, Chang et al., *Science* (1985) 228:93.

SUMMARY OF THE INVENTION

Peptide sequences capable of immunologically mimicking proteins encoded in the gag and/or env regions of the LAV/HTLV-III retrovirus are provided as reagents for use in the screening of blood and blood products for prior exposure to the retrovirus. The peptides are of at least 5 amino acids and can be used in various specific binding assays for the detection of antibodies to LAV/HTLV-III virus, for the detection of LAV/HTLV-III antigens, or as immunogens.

DESCRIPTION OF THE SPECIFIC EMBODIMENTS

For the purpose of this disclosure, a virus is considered to be the same as or equivalent to LAV/HTLV-III if it substantially fulfills the following criteria:

(a) The virus is tropic for T-lymphocytes, especially T-helper cells (CD4+, according to the international nomenclature defined in Bernard et al., eds. *Leucocyte Typing, N.Y.: Springer Verlag,* 1984);

(b) The virus is cytopathic for infected CD4+ cells (rather than transforming, as are HTLV-I and -II);

(c) The virus encodes an RNA-dependent DNA polymerase (reverse transcriptase) which is $Mg^{2+}$-dependent (optimum concentration 5 mM), has a pH optimum of 7.8, is not inhibitable by actinomycin D, and can employ oligo$(dT)_{12-18}$ as a primer for reverse transcription from its 3' LTR;

(d) The virus bands in a sucrose gradient at a density of approximately 1.16;

(e) The virus can be labeled with $[^3H]$-uridine;

(f) The virus is substantially cross-reactive immunologically with the proteins encoded by the gag and env regions of LAV/HTLV-III; and (g) The virus shares substantial nucleotide homology (approximately 75-100%) and amino acid sequence homology (approximately 75-100%) with LAV or HTLV-III.

Novel peptides are provided which immunologically mimic proteins encoded by the LAV/HTLV-III retrovirus, particularly proteins encoded by the gag and/or env regions of the viral genome. To accommodate strain-to-strain variations among different isolates, adjustments for conservative substitutions and selection among the alternatives where non-conservative substitutions are involved, may be made. These peptides can be used individually or together for detection of the virus or of antibodies to the virus in a physiological sample. Depending upon the nature of the test protocol, the peptides may be labeled or unlabeled, bound to a solid surface, conjugated to a carrier or other compounds, or the like.

The peptides of interest will be derived from the peptides encoded by the gag region or the env region. These peptides will be primarily derived from p55 or fragments thereof, e.g., p25 and p18, or gp110 and fragments thereof, e.g., gp43. These peptides will be given Roman numerals, but will also be given numerical designations which are arbitrarily associated with the manner in which they were produced. For the gag region, of particular interest are the coding regions extending from about base pair (bp) 900 to bp 1421, particularly from about bp 921 to bp 1010 or from about bp 1305 to about bp 1400 of the LAV/HTLV-III retrovirus, more particularly from about 936 to 995 (17) and 1320 to 1385 (15). (Numbering according to Wain-Hobson et al., supra.)

For the env region, the regions of particular interest will be those polypeptides encoded within the bp 7210 to bp 7815 regions, particularly within bp 7231 to bp 7794, more particularly within about bp 7246 through bp 7317 (36), bp 7516 through bp 7593 (39), bp 7708 through bp 7779 (23), bp 7630 through bp 7689 (40), bp 7498 through bp 7554 (56).

The peptides of interest will include at least five, sometimes six, sometimes eight, sometimes 12, usually fewer than about 50, more usually fewer than about 35, and preferably fewer than about 25 amino acids included within a sequence coded for by the LAV/HTLV-III retrovirus. In each instance, desirably the oligopeptide will be as small as possible, while still maintaining substantially all of the sensitivity of the larger peptide. In some instances it may be desirable to join two or more oligopeptides which are non-overlapping in the same peptide structure or as individual peptides, which separately or together provide equivalent sensitivity to the parent.

The peptides may be modified by introducing conservative or non-conservative substitutions in the peptides, usually fewer than 20 number percent, more usually fewer than 10 number percent of the peptides being exchanged. In those situations where regions are found to be polymorphic, it may be desirable to vary one or more particular amino acids to more effectively mimic the differing epitopes of the different retroviral strains.

It should be understood that the polypeptides employed in the subject invention need not be identical to any particular LAV/HTLV-III polypeptide sequence, so long as the subject compounds are able to provide for immunological competition with proteins of at least one of the strains of the LAV/HTLV-III retrovirus. Therefore, the subject polypeptides may be subject to various changes, such as insertions, deletions, and substitutions, either conservative or non-conservative, where such changes might provide for certain advantages in their use. By conservative substitutions is intended combinations such as gly, ala; val, ile, leu; asp, glu; asn, gln; ser, thr; lys, arg; and phe, tyr. Usually, the sequence will not differ by more than twenty percent from the sequence of at least one strain of an LAV/HTLV-III retrovirus except where additional amino acids may be added at either terminus for the purpose of providing an "arm" by which the peptides of this invention may be conveniently immobilized. The arms will usually be at least 1 amino acid and may be 50 or more amino acids, more often 1 to 10 amino acids.

In addition, one or two amino acids may be added to the termini of an oligopeptide or peptide to provide for ease of linking of peptides one to another, for coupling to a support or larger peptide, for reasons to be discussed subsequently, for modifying the physical or chemical properties of the peptide or oligopeptide, or the like.

Amino acids such as tyrosine, cysteine, lysine, glutamic or aspartic acid, or the like, may be introduced at the C- or N-terminus of the peptide or oligopeptide to provide for a useful functionality for linking.

In addition, the peptide or oligopeptide sequences may differ from the natural sequence by the sequence being modified by terminal-$NH_2$ acylation, e.g., acetylation, or thioglycolic acid amidation, terminal-carboxy amidation, e.g., ammonia, methylamine, etc. In some instances, these modifications may provide sites for linking to a support or other molecule.

The peptides and oligopeptides of interest will now be considered. The first peptides of interest will be derived from the gag region, particularly the protein referred to as p25.

The peptide I (15) encoded in the region bp 1320 to bp 1385 will have the following amino acid sequence, where oligopeptides included within the following sequence will include linear epitopes within such sequence:

(I) (15)

Y-Asp-Cys-Lys-Thr-Ile-Leu-Lys-Ala-Leu-Gly-Pro-Ala-Ala-Thr-Leu-Glu-Glu-Met-Met-Thr-Ala-Cys-X, where X is OH or $NH_2$, wherein the amino terminal Y, e.g., Tyr or Cys, if present, is added to facilitate coupling of the peptide to a protein carrier.

Preferably, this peptide will have no more than about 22 amino acids encoded by the LAV/HTLV III genome.

The next peptide II (17) will be encoded by the region extending from about bp 936 to bp 995 and will have the following sequence, where oligopeptides included within the following sequence will include linear epitopes within such sequence:

(II) (17)

Y-Leu-Lys-Glu-Thr-Ile-Asn-Glu-Glu-Ala-Ala-Glu-Trp-Asp-Arg-Val-His-Pro-Val-His-Ala-X, where X is OH or $NH_2$, wherein the amino terminal Y, has been defined previously.

Of particular interest is the oligopeptide IIa:

(IIa)

Y-Ala-Ala-Glu-Trp-Asp-Arg-Z-X, wherein X and Y have been defined previously and Z is a bond, an amino acid which provides a means of linking, e.g., cysteine, tyrosine, etc., or taken together with X provides a functional group which may be used for linking, e.g., an olefin as in allyl or maleimidyl, dithio, etc.

The next polypeptides of interest will be those derived from the env region, from gp110 (110 kDal).

The next peptide of interest, III, will be encoded by the region extending from about bp 7246 through bp 7317 and while coming within the general limitations indicated previously, will preferably have no more than 24 amino acids encoded by the LAV/HTLV III genome.

The peptide of interest will generally have the following amino acid sequence, where oligopeptides included within the following sequence will include linear epitopes within such sequence:

(III) (36)

Val-Lys-Ile-Glu-Pro-Leu-Gly-Val-Ala-Pro-Thr-Lys-Ala-Lys-Arg-Arg-Val-Val-Gln-Arg-Glu-Lys-Arg-Ala-Z-X, where X is OH or $NH_2$, wherein the carboxy terminal Z, e.g., Cys, if present, is an amino acid added to facilitate coupling of the peptide to a protein carrier.

Of particular interest is where 6, conveniently up to 4, of the naturally occurring C-terminal amino acids are deleted or substituted.

Oligopeptides contained within the above sequence of particular interest include:

(IIIa) (49)

Y-Arg-Val-Val-Gln-Arg-Glu-Lys-Arg-Z-X (IIIb) (50)

Y-Pro-Thr-Lys-Ala-Lys-Arg-Arg-Val-Val-Gln-Arg-Glu-Lys-Arg-X.

The next peptide, IV (56), will be encoded by the region extending from about bp 7498 to bp 7554, where oligopeptides included within the following sequence will include linear epitopes within such sequence:

(IV) (56)

Ile-Lys-Gln-Leu-Gln-Ala-Arg-Ile-Leu-Ala-Val-Glu-Arg-Tyr-Leu-Lys-Asp-Gln-Gln-Z-X, wherein X, Y and Z have been defined previously.

Oligopeptides contained within the above sequence of particular interest include:

(IVa) (56/39)

Y-Arg-Ile-Leu-Ala-Val-Glu-Arg-Tyr-Leu-Lys-Asp-Gln-Gln-Z-X

The next peptide of interest, V (39), will be encoded by the region from about bp 7516 through bp 7593 and has the following amino acid sequence, where oligopeptides included within the following sequence will include linear epitopes within such sequence:

(V) (39)

Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu-Ile-Cys-X, where X is OH or $NH_2$.

The next peptide, VI (40), will be encoded by the region extending from about bp 7630 to 7689 where oligopeptides included within the following sequence will include linear epitopes within such sequence:

(VI) (40)

Y-Lys-Ser-Leu-Glu-Gln-Ile-Trp-Asn-Asn-Met-Thr-Trp-Met-Glu-Trp-Asp-Arg-Glu-Ile-Asn-Z-X, wherein Y, X and Z have been defined previously.

The next peptide of interest, VII (23), will be encoded by the region extending from about bp 7708 through bp 7779. This peptide will include any oligopeptides coding for linear epitopes within the following amino acid sequence:

(VII) (23)

Y-His-Ser-Leu-Ile-Glu-Glu-Ser-Gln-Asn-Gln-Gln-Glu-Lys-Asn-Glu-Gln-Glu-Leu-Leu-Glu-Leu-Asp-Lys-Trp-Z-X, wherein X, Y and Z have been defined previously.

Of particular interest is the use of the mercaptan group of cysteines or thioglycolic acids used for acylating terminal amino groups or the like for linking two of the peptides or oligopeptides or combinations thereof by a disulfide linkage or a longer linkage. To achieve this, compounds may be employed having bis-haloacetyl groups, nitroarylhalides, or the like, where the reagents are specific for thio groups. Thus, the linking between the two mercapto groups of the different peptides or oligopeptides may be a single bond or a linking group of at least two, usually at least four, and not more than about 16, usually not more than about 14 carbon atoms. Of particular interest, is where a member of a sequence from the gag region is linked to a member from the env region. These chimeric peptides which may include non-amino acid linkages, may be further modified as will be described for the peptides and oligopeptides.

The subject peptides may be employed linked to a soluble macromolecular (e.g., ≧5 kDal) carrier. Conveniently, the carrier may be a poly(amino acid), either naturally occurring or synthetic, to which antibodies are unlikely to be encountered in human serum. Illustrative polypeptides include poly-L-lysine, bovine serum albumin, keyhole limpet hemocyanin, bovine gamma globulin, etc. The choice is primarily one of convenience and availability.

With such conjugates, there will be at least one molecule of at least one subject peptide per macromolecule and not more than about 1 per 0.5 kDal, usually not more than about 1 per 2 kDal of the macromolecule. One or more different peptides may be linked to the same macromolecule.

The manner of linking is conventional, employing such reagents as p-maleimidobenzoic acid, p-methyldithiobenzoic acid, maleic acid anhydride, succinic acid anhydride, glutaraldehyde, etc. The linkage may occur at the N-terminus, C-terminus or at a site intermediate the ends of the molecule. The subject peptide may be derivatized for linking, may be linked while bound to a support, or the like.

The compounds may be employed as labeled or unlabeled compounds depending upon their use. (By label is intended a molecule which provides, directly or indirectly, a detectable signal.) Various labels may be employed, such as radionuclides, enzymes, fluorescers, chemiluminescers, enzyme substrates, cofactors or inhibitors, particles, e.g., magnetic particles, combinations of ligands and receptors, e.g., biotin and avidin, or the like. In addition, the polypeptides may be modified in a variety of ways for binding to a surface, e.g., microtiter plate, glass beads, chromatographic surface, e.g., paper, cellulose, silica gel, or the like. The particular manner in which the polypeptides are joined to another compound or surface is conventional and finds ample illustration in the literature. See, for example, U.S. Pat. Nos. 4,371,515; 4,487,715; and patents cited therein.

Various assay protocols may be employed for detecting the presence of either antibodies to retroviral proteins or retroviral proteins themselves. Of particular interest is using the peptide as the labeled reagent, where the label allows for a detectable signal, or binding the peptide, either directly or indirectly to a surface, where antibody to the peptide in the sample will become bound to the peptide on the surface. The presence of human antibody bound to the peptide can then be detected by employing a xenogeneic antibody specific for human immunoglobulin, normally both human IgM and IgG, or a labeled protein specific for immune complexes, e.g., Rf factor or *S. aureus* protein A.

Various heterogeneous protocols may be employed, either competitive or non-competitive. Peptide may be bound to a surface or support ("support") and labeled antibody allowed to compete with antibody in the sample for the limited amount of bound peptide. The amount of label bound to the support would be related to the amount of competitive antibody in the sample.

Antibody could be bound to the support and the sample combined with labeled peptide. After contact of the reaction mixture with the bound antibody, the amount of label bound to the support would relate to the amount of cognate antibody in the sample.

Xenogeneic anti-human antibody, e.g., antibodies to the $F_c$ of IgG and IgM (immunoglobulins), could be bound to a support. The sample would be contacted with the immunoglobulins and labeled peptide, whereby the amount of labeled peptide bound to the support would be indicative of the presence of the cognate antibodies.

Alternatively, homogeneous assays can be employed where the peptide is bound to an enzyme, fluorescer, or other label, where the binding of antibody to the peptide results in being able to discriminate between the label involved with a specific binding pair complex and label which is not involved in the complex. For assays involving such techniques, see for example U.S. Pat. Nos. 3,817,837; 3,850,752; 3,901,654; 3,935,074; 3,984,533; 3,996,345; 4,034,074; and 4,098,876, whose disclosures are incorporated herein by reference.

As an illustration of the subject invention the subject peptides may be conjugated to a fluorescent molecule, such as fluorescein, rhodamine or umbelliferone. Various techniques may be used for detecting complex formation with antibodies, e.g., fluorescence polarization. In this assay the fluorescence polarization is different between complexed and uncomplexed peptide conjugate. Apparatuses are available for measuring changes in fluorescence polarization, e.g., TDx supplied by Abbott Laboratories, Chicago, Ill.

Illustrative of an assay technique is the use of sample containers, e.g., microtiter plate wells, where the subject polypeptides or conjugates thereof are adhered to the container bottom and/or walls either covalently or non-covalently. The sample, normally human blood or serum diluted in an appropriately buffered medium, is added to the container and a sufficient time allowed for complex formation between the polypeptide(s) and any cognate antibodies in the sample. The supernatant is removed and the container washed to remove non-specifically bound proteins.

A labeled specific binding protein which specifically binds to the complex is employed for detection. To the container may be added xenogeneic antisera to human immunoglobulin, particularly anti-(human IgM and IgG) in an appropriately buffered medium. The xenogeneic antisera will normally be labeled with a detectable label, e.g., radionuclide or enzyme. Instead of antisera, proteins specific for the immune complex may be employed, e.g., *S. aureus* protein A. The label may then be detected. For example, with an enzyme, after removal of non-specifically bound enzyme label, a developer solution is added. The developer solution will contain an enzyme substrate and possibly enzyme cofactors, chromogens, etc., which, upon reaction, provide a colored or fluorescent product which may be detected colorimetrically or fluorimetrically, respectively.

The peptides can be prepared in a wide variety of ways. The peptides, because of their relatively short size, may be synthesized in solution or on a solid support in accordance with conventional techniques. Various automatic synthesizers are commercially available today and can be used in accordance with known protocols. See, for example, Stewart and Young, Solid Phase Peptide Synthesis, 2nd ed., Pierce Chemical Co., 1984; and Tam et al., *J. Am. Chem. Soc.* (1983) 105:6442.

Alternatively, hybrid DNA technology may be employed where a synthetic gene may be prepared by employing single strands which code for the polypeptide or substantially complementary strands thereof, where the single strands overlap and can be brought together in an annealing medium so as to hybridize. The hybridized strands may then be ligated to form the complete gene and by choice of appropriate termini, the gene may be inserted into expression vectors, which are readily available today. See, for example, Maniatis et al., Molecular Cloning, A Laboratory Manual, CSH, Cold Spring Harbor Laboratory, 1982. Or, the region of the viral genome coding for the peptide may be cloned by conventional recombinant DNA techniques and expressed (see Maniatis, supra).

DNA coding sequences which may be used for expressing peptides I–VII are:

I (TAT)GATTGTAAGACTATTTAAAAG-CATTGGGACCAG CAGCTACAC-TAGAAGAAATGATGACAGCATGT;

II (TGT)TTAAAAGAGACCATCAATGAG-GAAGCTGCAGAATGGGAT AGAGTGCATC-CAGTGCATGCA;

III GTAAAAATTGAACCATTAGGAGTAG-CACCCACCAAGGCA AAGAGAAGAGTGGT-GCAGAGAGAAAAAAGAGCA(TGT);

IV ATCAAGCAGCTCCAGG-CAAGAATCCTGGCTGTGGAAAGA TACC-TAAAGGATCAACAG(TGT);

V AGAATCCTGGCTGTGGAAAGATACC-TAAAGGATCAACAG CTCCTGGGGATTTGGGGTTGCTCT-GGAAAACTCATTTGC;

VI (TGT)AAATCTCTGGAACAGATTT-GGAATAACATGACCTGGATG GAGTG-GGACAGAGAAATTAAC(TGT);

VII (TGT)CATTCCTTAATTGAAGAATC-GCAAAACCAGCAAGAAAAG AAT-GAACAAGAATTATTGGAAT-TAGATAAATGG(GGA)

Fragments from these sequences may be employed for expression of peptide fragments, conservative base changes can be made, where the modified codon(s) code for the same amino acid(s), or non-conservative changes in the coding sequence may be made, where the resulting amino acid may be a conservative or non-conservative change.

The coding sequence may be extended at either the 5′- or 3′-terminus or both termini to extend the peptide, while retaining its epitopic site. The extension may provide for an arm for linking, e.g., to a label, such as an enzyme, for joining two or all of the peptides together in the same chain, for providing antigenic activity, or the like.

For expression, the coding sequence will be provided with start and stop codons, promoter and terminator regions and usually a replication system to provide an expression vector for expression in a cellular host, e.g., prokaryotic or eukaryotic, bacterial, yeast, mammal, etc.

The sequences by themselves, fragments thereof, or larger sequences, usually at least 15 bases, preferably at least 18 bases, may be used as probes for detection of retroviral RNA or proviral DNA. Numerous techniques are described, such as the Grunstein-Hogness technique, Southern technique, Northern technique, dot-blot, improvements thereon, as well as other methodology. See, for example, WO 83/02277 and Berent et al., Biotechniques (1985) 3:208.

Conveniently, the polypeptides may be prepared as fused proteins, where the polypeptide may be the N- or C-terminus of the fused polypeptide. The resulting fused protein could be used directly by itself as the reagent or the subject polypeptide may be cleaved from all or a portion of the remaining sequence of the fused protein. With a polypeptide where there are no internal methionines, by introducing a methionine at the fusion site, the polypeptide may be cleaved employing cyanogen bromide. Where there is an internal methionine, it would be necessary to provide for a proteolytic cleavage site, e.g., poly-lysine and/or -arginine or combinations thereof, or the internal methionine could be substituted with an amino acid such as leucine and an N-terminal methionine added for cyanogen bromide cleavage. A wide variety of proteases, including dipeptidases, are well known and the appropriate processing signal could be introduced at the proper site. The processing signal may have tandem repeats so as to insure cleavage, since the presence of one or more extraneous amino acids will not interfere with the utility of the subject polypeptides.

Depending upon the nature of the assay, the physiological sample, e.g., saliva, blood, plasma, or serum, may be pretreated by dilution into an assay medium, which will usually be an aqueous buffered medium employing one of a variety of buffers, such as phosphate, tris, or the like. A preferred diluent is blotto (5% w/v nonfat dry milk, 0.01% thimerosol, 0.01% Antifoam A in 0.01 M sodium phosphate, pH 7.2, and 0.15 M NaCl). Usually the pH will be in the range of about 6 to 9. The sample will then be combined with the reagent in accordance with the appropriate protocol and sufficient time allowed for binding. Where a heterogeneous system is used, usually the stages will be followed by washes, to minimize non-specific binding. At the end of the procedure, the label will be detected in accordance with conventional ways.

Besides the use of the subject peptides and their analogs in assays, the subject peptides may also find use by themselves or in combination in vaccines. The peptides may be formulated in a convenient manner, generally at concentrations in the range of 1 μg to 20 mg/kg of host. Physiologically acceptable media may be used as carriers, such as sterile water, saline, phosphate buffered saline, and the like. Adjuvants may be employed, such as aluminum hydroxide gel, or the like. Administration may be by injection, e.g., intramuscularly, peritoneally, subcutaneously, intravenously, etc. Administration may be one or a plurality of times, usually at one to four week intervals.

The following examples are offered by way of illustration and not by way of limitation.

EXPERIMENTAL

Peptide I was assembled on a t-butyloxy-carbonyl (BOCD)-methylbenzylcysteine-phenyl-acetamidomethyl (PAM) polystyrene/divinylbenzene resin (Applied Biosystems, Inc., Foster City, Calif.). Symmetrical anhydride couplings were carried out in an Applied Biosystems 430A synthesizer. Benzyl based side chain protection and BOC alpha-amine protection were used. Tryptophan was protected by the formyl moiety and methionine by its sulfoxide, both protecting groups being removed by conventional procedures.

Peptide III was assembled on a benzhydrylamine polystyrene/divinylbenzene resin in a Beckman 990 peptide synthesizer (Beckman Instruments, La Brea, Calif.). Benzyl based side chain protection and BOC alpha-amine protection were used. All the residues were added by the direct dicyclohexylcarbodiimide method, except for glutamine which was coupled as the hydroxybenzotriazole ester.

Peptide V was synthesized on a benzhydrylamine resin as described for peptide III with asparagine also being coupled as the ester.

The peptides were radiolabeled by acetylating the amino terminus with $^3$H-acetic acid and an excess of dicyclohexylcarbodiimide. The peptides were deprotected and cleaved from the resin by the Tam "low-high" HF protocol (Tam et al., supra). Peptides III and V were extracted from the resin in 5% acetic acid and subjected to gel filtration chromatography in 5% acetic acid. Peptide I was extracted in 0.5 M ammonium carbonate/0.001 M dithiothreitol (DTT) and chromatographed in 0.05 M ammonium carbonate/0.005 M β-mercaptoethanol. The fractions containing tritiated peptide were pooled and lyophilized. The integrity of the synthetic products was assured by ninhydrin monitoring after each coupling and by analytical reverse phase chromatography and amino acid analysis.

The peptides synthesized above were conjugated to bovine serum albumin (BSA) which had been derivatized with N-succinimidyl-4-(N-maleimidomethyl)cyclohexane-1-carboxylate (SMCC), essentially as described by Ishikawa et al., *J. of Immunoassay* (1983) 4:209.

To 2 ml of a BSA solution (20 mg/ml in 0.1 M potassium phosphate, pH 7.0) at 30° C. was added 1.5 ml of an SMCC solution (8 mg/ml in dimethylformamide). The mixture was stirred magnetically for 1 hr, after which it was centrifuged to remove any precipitated albumin. The clarified mixture was then subjected to gel filtration on Sephadex G-25 equilibrated in 0.1 M potassium phosphate, pH 6.0. The protein-containing fractions, as determined by their absorbance at 280 nm, were pooled and stored frozen at −70° C. until needed.

The peptides synthesized above were dissolved in 0.1 M sodium phosphate, pH 8.0 to a concentration of 5 mg/ml (peptide III), 8 mg/ml (peptide I) or 1.6 mg/ml (peptide V). To 1.5 ml of each solution was added 2 mg of solid DTT. The solutions were stirred for 30 min at 30° C., after which they were subjected to gel filtration chromatography on Sephadex G-10, equilibrated in 0.1 M potassium phosphate, pH 6.0. The tritium-containing fractions, as determined by scintillography of aliquots, were pooled and mixed with 1 ml (0.5 ml for peptide V) of SMCC-derivatized BSA. The resultant mixtures were stirred at 30° C. for 12 hr and then dialyzed exhaustively against water.

The other peptides were prepared in accordance with the procedures described above and conjugated to BSA in accordance with the above described procedures. The ratio of peptide to BSA was determined by employing radiotracers in accordance with conventional ways.

| | mols peptide / mol BSA |
|---|---|
| I (15) | 14 |
| II (17) | 5 |
| III (36) | 9 |
| IV (56) | 17 |
| V (39) | 6 |
| VI (40) | 18 |
| VII (23) | 30* |

*may be erroneous and could be as high as 55.

SUMMARY OF TABLE 1

Table 1 gives ELISA results for all petpides that are immunoreactive.

Peptides 49 and 50 are part of peptide 36.

Peptide 56 partially overlaps peptide 39.

Peptide 49-BSA reactive with 10/10 positve sera; not reactive with 2/2 negative sera.

Peptide 50-BSA reactive with 10/10 positive sera; not reactive with 2/2 negative sera.

Peptide 56-BSA reactive with 10/10 positive sera; not reactive wtih 2/2 negative sera.

Peptide 40-BSA reactive with 10/10 positive sera; not reactive with 2/2 negative sera.

Peptide 23-BSA reactive with 10/10 positive sera; not reactive with 2/2 negative sera.

Peptide 15-BSA reactive with 10/10 positive sera; not reactive with 2/2 negative sera.

Peptide 36-BSA reactive with 9/10 positive sera; not reactive with 2/2 negative sera.

In a larger panel, peptide 56 which partially overlaps peptide 39, is not reactive with all sera that are reactive with peptide 39. This suggests that there are at least two reactive epitopes within peptide 39 or that peptides 39 and 56 contain non overlapping reactive epitopes.

Peptide 23 (both conjugated to BSA and unconjugated) was further tested against a larger panel of sera (23 positives, 8 negatives) and displays a sensitivity of 80-90%.

SUMMARY OF TABLE 2

Table 2 shows that two of the peptides derived from the gag region (#15 and #17) are reactive with LAV seropositive sera that are poorly reactive or unreactive with peptide 39. This supports the use of a combination of gag and env peptides to produce a more sensitive assay.

SUMMARY OF TABLE 3

Table 3 compares results obtained with peptides 15-BSA and 39 with results obtained with these peptides physically mixed (15-BSA +39) or chemically combined (thiol-oxidized 15+39).

The result obtained when positive samples are assayed with either the physical or chemical combination of peptides 15 and 39 is generally higher than that obtained with either peptide alone. This is clearly demonstrated with samples 126, 131, 135, 138 and 1296.

TABLE 1

COMPARISON OF PEPTIDES WITH A WHOLE VIRUS LYSATE IN AN ELISA ASSAY FOR THE DETECTION OF ANTIBODIES TO LAV

| Positive Sera | Diagnosis | ELISA Using Whole Virus Lysate[1] | Confirmed as Serpositive[2] | BSA-Pep15 | BSA-Pep36 | BSA-Pep49 | BSA-Pep50 | Pep39 | BSA-Pep56 | BSA-Pep40 | BSA-Pep23 | Pep23 |
|---|---|---|---|---|---|---|---|---|---|---|---|---|
| 155 | LAS and/or homosexual | 1.069 | yes | 0.525 | 1.679 | 0.955 | 1.678 | 1.167 | 1.675 | 0.603 | 1.640 | 0.111 |
| 124 | LAS and/or homosexual | 1.189 | yes | 1.329 | 1.465 | 1.334 | 2.207 | 1.073 | 1.842 | 1.462 | 2.117 | 2.127 |
| 138 | LAS and/or homosexual | 1.302 | yes | 0.378 | 0.159 | 0.204 | 0.374 | 0.514 | 0.643 | 0.774 | 0.960 | 0.106 |
| 133 | LAS and/or homosexual | 1.250 | yes | 0.365 | 0.567 | 0.409 | 0.581 | 1.036 | 0.627 | 1.297 | 2.077 | N.D. |
| 131 | LAS and/or homosexual | 1.220 | yes | 0.411 | 0.272 | 0.225 | 0.595 | 0.448 | 1.679 | 1.209 | 1.621 | 0.949 |
| 134 | LAS and/or homosexual | 1.050 | yes | 0.559 | 0.712 | 0.729 | 0.293 | 1.619 | 2.170 | 0.567 | 1.705 | 1.552 |
| 153 | LAS and/or homosexual | 2.000 | yes | 0.467 | 0.548 | 1.011 | 0.591 | 1.314 | 1.324 | 0.734 | 0.970 | 0.524 |
| 157 | LAS and/or homosexual | 1.349 | yes | 0.366 | 0.321 | 0.148 | 0.427 | 1.326 | 2.179 | 1.153 | 2.017 | 1.158 |
| Y-1/CDC | LAS and/or homosexual | 2.000 | yes | 2.109 | 1.022 | 1.547 | 1.928 | 1.305 | 2.115 | 1.257 | 1.565 | 0.762 |
| 501 | LAS and/or homosexual | 1.109 | yes | 2.374 | 1.168 | 1.938 | 2.209 | 1.167 | 1.170 | 0.625 | 0.467 | 0.059 |
| 1892 | Healthy heterosexual | n.d. | n.d.[4] | 0.128 | 0.113 | 0.119 | 0.124 | 0.045 | 0.143 | 0.141 | 0.253 | 0.034 |
| 639 | Healthy heterosexual | 0.123 | not seropositive | 0.159 | 0.142 | 0.102 | 0.186 | 0.038 | 0.355 | 0.251 | 0.286 | 0.024 |

TABLE 2

COMPARISON OF GAG PEPTIDES WITH PEPTIDE 39 IN AN ELISA ASSAY FOR THE DETECTION OF ANTIBODIES TO LAV

| Serum No. | Diagnosis | Whole Virus Lysate[1] | Confirmed as Seropositive[2] | 17-BSA | 15-BSA | 39 |
|---|---|---|---|---|---|---|
| 1296 | Blood Donor | 2.01 | yes | 0.633 | 0.65 | 0.11 |
| 501 | Unknown | 1.109 | yes | 0.18 | 2.04 | 2.15 |
| 129 | LAS and/or homosexual | 1.08 | yes | 0.62 | 0.49 | 0.42 |
| 154 | LAS and/or homosexual | 1.41 | yes | 0.26 | 0.26 | 0.35 |
| 7 | LAS and/or homosexual | 2.00 | yes | 0.79 | 1.02 | 0.22 |
| 641 | Healthy heterosexual | 0.20 | n.d. | 0.22 | 0.19 | 0.04 |
| 639 | Healthy | 0.12 | n.d. | 0.20 | 0.16 | 0.05 |

TABLE 2-continued

COMPARISON OF GAG PEPTIDES WITH PEPTIDE 39 IN AN ELISA ASSAY FOR THE DETECTION OF ANTIBODIES TO LAV

| Serum No. | Diagnosis | Whole Virus Lysate[1] | Confirmed as Seropositive[2] | 17-BSA | 15-BSA | 39 |
|---|---|---|---|---|---|---|
| | heterosexual | | | | | |

TABLE 3

COMPARISON OF PEPTIDES 15 AND 39 INDIVIDUALLY WITH PEPTIDES 15 AND 39 PHYSICALLY OR CHEMICALLY COMBINED IN AN ELISA ASSAY FOR THE DETECTION OF ANTIBODIES TO LAV

| Serum No. | Diagnosis | Whole Virus Lysate[1] | Confirmed as Seropositive[2] | 15-BSA | 39 | 15-BSA 39 | Thiol-oxidized 15 + 39 |
|---|---|---|---|---|---|---|---|
| 133 | LAS and/or homosexual | 1.250 | yes | 0.13 | 1.02 | >2 | 1.88 |
| 134 | LAS and/or homosexual | 1.050 | yes | 0.21 | 1.62 | >2 | 2.27 |
| 135 | LAS and/or homosexual | 1.310 | yes | 0.25 | 0.32 | 1.93 | 1.48 |
| 138 | LAS and/or homosexual | 1.302 | yes | 0.13 | 0.51 | 1.65 | 0.91 |
| 153 | LAS and/or homosexual | 2.000 | yes | 0.16 | 1.32 | n.d. | 1.89 |
| 154 | LAS and/or homosexual | 1.41 | yes | 0.19 | 0.35 | n.d. | 1.35 |
| 155 | LAS and/or homosexual | 1.069 | yes | 0.29 | 1.17 | n.d. | 1.83 |
| 157 | LAS and/or homosexual | 1.349 | yes | 0.14 | 1.33 | n.d. | n.d. |
| 666 | Unknown | 2.000 | yes | 1.60 | 1.39 | >2 | 2.01 |
| 1296 | Blood Donor | 2.00 | yes | 0.65 | 0.11 | 0.99 | 0.16 |
| 633 | Healthy heterosexual | 0.222 | not sero-positive | 0.09 | 0.05 | n.d. | n.d. |
| 637 | Healthy heterosexual | 0.097 | not sero-positive | 0.13 | 0.04 | 0.42 | n.d. |
| 639 | Healthy heterosexual | 0.123 | not sero-positive | 0.12 | 0.04 | 0.22 | 0.11 |
| 641 | Healthy heterosexual | 0.199 | not sero-positive | 0.18 | 0.03 | 0.49 | 0.13 |
| 501 | Positive control | 1.109 | yes | 1.39 | 1.17 | >2.0 | 1.77 |
| Y-1 CDC | Positive control pool | 2.000 | yes | 1.02 | 1.30 | >2.0 | 2.02 |
| 120 | LAS[3] and/or homosexual | 1.540 | yes | 0.19 | 1.37 | n.d. | n.d. |
| 121 | LAS and/or homosexual | 1.483 | yes | 0.09 | 1.51 | >2.0 | 1.96 |
| 122 | LAS and/or homosexual | 1.283 | yes | 0.14 | 1.88 | >2.0 | 2.33 |
| 124 | LAS and/or homosexual | 1.189 | yes | 0.60 | 1.06 | n.d. | n.d. |
| 125 | LAS and/or homosexual | 1.232 | yes | 0.18 | 1.53 | n.d. | n.d. |
| 126 | LAS and/or homosexual | 1.233 | yes | 0.24 | 0.51 | >2 12 | 1.5 |
| 127 | LAS and/or homosexual | 1.046 | yes | 0.25 | 1.52 | n.d. | n.d. |
| 128 | LAS and/or homosexual | 1.284 | yes | 0.09 | 1.07 | n.d. | n.d. |
| 129 | LAS and/or homosexual | 1.081 | yes | 0.33 | 0.42 | n.d. | n.d. |
| 130 | LAS and/or homosexual | 0.912 | yes | 0.28 | 1.17 | n.d. | n.d. |
| 131 | LAS and/or homosexual | 1.220 | yes | 0.14 | 0.45 | >2 | 1.22 |
| 132 | LAS and/or homsexual | 1.237 | yes | 0.15 | 1.24 | >2 | 1.91 |
| 667 | Healthy heterosexual | 0.095 | n.d. | 0.15 | 0.04 | 0.42 | n.d. |
| 1890 | Healthy heterosexual | n.d. | n.d. | 0.15 | 0.05 | 0.39 | 0.15 |
| 1891 | Healthy heterosexual | n.d. | n.d. | 0.17 | 0.05 | 0.31 | 0.12 |
| 1892 | Healthy | n.d. | n.d. | 0.08 | 0.05 | 0.18 | 0.07 |

TABLE 3-continued

| COMPARISON OF PEPTIDES 15 AND 39 INDIVIDUALLY WITH PEPTIDES 15 AND 39 PHYSICALLY OR CHEMICALLY COMBINED IN AN ELISA ASSAY FOR THE DETECTION OF ANTIBODIES TO LAV | | | | | | | |
|---|---|---|---|---|---|---|---|
| Serum No. | Diagnosis | Whole Virus Lysate[1] | Confirmed as Seropositive[2] | 15-BSA | 39 | 15-BSA 39 | Thiol-oxidized 15 + 39 |
| | heterosexual | | | | | | |

FOOTNOTES TO TABLES 1-3
[1]Prepared as described in U.K. application Serial No. 83/24800, filed September 15, 1983.
[2]Radiolabeled LAV antigens were disrupted in RIPA buffer (Gilead et al., Nature (1976) 254:263) and then were reacted with human serum. The resultant immune complexes were separated by binding to a *Staphylococcus aureus* adsorbent (Kessler, J. Immunology (1975) 115:1617) followed by multiple washings. Immuneprecipitated antigens were analyzed by SDS polyacrylamide gel electrophoresis (Laemmli, Nature (1970) 227:680) followed by fluorography. Presence of either a p25 or gp43 band was considered necessary and sufficient to confirm a sample as seropositive.
[3]LAS = lymphadenopathy syndrome.
[4]N.D. = not determined.

It is evident from the foregoing results that by employing one or a combination of peptides of the subject invention, a sensitive accurate test for the presence of antibodies to AIDS is provided. The subject peptides can be used by themselves or in combination with a screening assay or confirmatory assay, where the complete lysate or complete antigens may be employed as an independent procedure. Furthermore, because of the specificities of the peptides, one would anticipate that the DNA sequences coding for the peptides would also find similar specificity in a DNA hybridization assay. Thus, the subject invention allows for the detection of patients who have been exposed to the retroviral etiologic agent of lymphadenopathy syndrome and/or AIDS.

Although the foregoing invention has been described in some detail by way of illustration and example for purposes of clarity of understanding, it will be obvious that certain changes and modifications may be practiced within the scope of the appended claims.

What is claimed is:

1. A peptide of the formula:

(I)

Y-Asp-Cys-Lys-Thr-Ile-Leu-Lys-Ala-Leu-Gly-Pro-Ala-Ala-Thr-Leu-Glu-Glu-Met-Met-Thr-Ala-Cys-X, where X is OH or $NH_2$, and Y, if present, is an amino acid added to facilitate coupling, N-terminal acetylated I, and I linked to a peptide or protein of at least 5,000 molecular weight, which peptide or protein does not normally bind to antibodies present in a human host.

2. A peptide of the formula:

(II)

Y-Leu-Lys-Glu-Thr-Ile-Asn-Glu-Glu-Ala-Ala-Glu-Trp-Asp-Arg-Val-His-Pro-Val-His-Ala-X, where X is OH or $NH_2$, and Y, if present, is an amino acid added to facilitate coupling, N-terminal acetylated II, and II linked to a peptide or protein of at least 5,000 molecular weight, which peptide or protein does not normally bind to antibodies present in a human host.

3. A peptide of the formula:

(III)

Val-Lys-Ile-Glu-Pro-Leu-Gly-Val-Ala-Pro-Thr-Lys-Ala-Lys-Arg-Arg-Val-Val-Gln-Arg-Glu-Lys-Arg-Ala-Z-X, where X is OH or $NH_2$, and Z, if present, is an amino acid added to facilitate coupling, N-terminal acetylated III, and III linked to a peptide or protein of at least 5,000 molecular weight, which peptide or protein does not normally bind to antibodies present in a human host.

4. A peptide of the formula:

(IV) (56)

Ile-Lys-Gln-Leu-Gln-Ala-Arg-Ile-Leu-Ala-Val-Glu-Arg-Tyr-Leu-Lys-Asp-Gln-Gln-Z-X, where X is OH or $NH_2$, and Z, if present, is an amino acid added to facilitate coupling, N-terminal acetylated IV, and IV linked to a peptide or protein of at least 5,000 molecular weight, which peptide or protein does not normally bind to antibodies present in a human host.

5. A peptide of the formula:

(V) (39)

Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu-Ile-Cys-X, where X is OH or $NH_2$, N-terminal acetylated V, and V linked to a peptide or protein of at least 5,000 molecular weight, which peptide or protein does not normally bind to antibodies present in a human host.

6. A peptide of the formula:

(VI) (40)

Y-Lys-Ser-Leu-Glu-Gln-Ile-Trp-Asn-Asn-Met-Thr-Trp-Met-Glu-Trp-Asp-Arg-Glu-Ile-Asn-Z-X, where X is OH or $NH_2$, and each of Y and Z, if present, is an amino acid added to facilitate coupling, N-terminal acetylated VI, and VI linked to a peptide or protein of at least 5,000 molecular weight, which peptide or protein does not normally bind to antibodies present in a human host.

7. A peptide of the formula:

(VII) (23)

Y-His-Ser-Leu-Ile-Glu-Glu-Ser-Gln-Asn-Gln-Gln-Glu-Lys-Asn-Glu-Gln-Glu-Leu-Leu-Glu-Leu-Asp-Lys-Trp-Z-X, where X is OH or $NH_2$, and each of Y and Z, if present, is an amino acid added to facilitate coupling, N-terminal acetylated VII, and VII linked to a peptide or protein of at least 5,000 molecular weight, which peptide or protein does not normally bind to antibodies present in a human host.

* * * * *